US009648881B2

(12) United States Patent
Yamada et al.

(10) Patent No.: US 9,648,881 B2
(45) Date of Patent: May 16, 2017

(54) HERBICIDAL COMPOSITION COMPRISING NICOSULFURON OR ITS SALT AND S-METOLACHLOR OR ITS SALT

(71) Applicant: ISHIHARA SANGYO KAISHA, LTD., Osaka (JP)

(72) Inventors: Ryu Yamada, Kusatsu (JP); Hiroyuki Okamoto, Kasatsu (JP); Takashi Terada, Kusatsu (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/368,848

(22) PCT Filed: Dec. 26, 2012

(86) PCT No.: PCT/JP2012/084281
§ 371 (c)(1),
(2) Date: Jun. 26, 2014

(87) PCT Pub. No.: WO2013/100178
PCT Pub. Date: Jul. 4, 2013

(65) Prior Publication Data
US 2015/0011391 A1     Jan. 8, 2015

(30) Foreign Application Priority Data

Dec. 27, 2011 (JP) ................................. 2011-285654

(51) Int. Cl.
| A01N 47/36 | (2006.01) |
| A01N 37/22 | (2006.01) |
| A01N 43/70 | (2006.01) |
| A01N 37/18 | (2006.01) |
| A01N 41/10 | (2006.01) |
| A01N 43/40 | (2006.01) |

(52) U.S. Cl.
CPC ............. *A01N 47/36* (2013.01); *A01N 37/18* (2013.01); *A01N 37/22* (2013.01); *A01N 41/10* (2013.01); *A01N 43/40* (2013.01); *A01N 43/70* (2013.01)

(58) Field of Classification Search
CPC .............................. A01N 47/36; A01N 37/22
See application file for complete search history.

(56) References Cited

U.S. PATENT DOCUMENTS

| 5,002,606 | A | * | 3/1991 | Moser .................. A01N 37/22 504/149 |
| 5,741,756 | A | | 4/1998 | Shribbs |
| 5,849,665 | A | | 12/1998 | Gut et al. |
| 5,981,432 | A | | 11/1999 | Hudetz et al. |
| 6,017,851 | A | | 1/2000 | Gut et al. |
| 6,046,134 | A | | 4/2000 | De Gennaro et al. |
| 8,298,993 | B2 | | 10/2012 | Dunne et al. |
| 8,492,310 | B2 | | 7/2013 | Kikugawa et al. |
| 8,846,571 | B2 | | 9/2014 | Kikugawa et al. |
| 2004/0033897 | A1 | | 2/2004 | Haas |
| 2004/0167033 | A1 | | 8/2004 | Johnson et al. |
| 2007/0142228 | A1 | | 6/2007 | Haas |
| 2009/0264292 | A1 | | 10/2009 | Yoshii et al. |
| 2010/0285959 | A1 | | 11/2010 | Armel et al. |
| 2011/0143938 | A1 | | 6/2011 | Fowler et al. |
| 2011/0166023 | A1 | | 7/2011 | Nettleton-Hammond et al. |
| 2011/0190126 | A1 | | 8/2011 | Hall et al. |
| 2011/0263427 | A1 | | 10/2011 | Kikugawa et al. |
| 2015/0087515 | A1 | | 3/2015 | Yamada et al. |
| 2016/0174561 | A1 | | 6/2016 | Yamada et al. |

FOREIGN PATENT DOCUMENTS

| CN | 1826894 | A | 9/2006 |
| CN | 101142914 | | 3/2008 |
| CN | 101292663 | | 10/2008 |
| EP | 1388285 | A2 | 2/2004 |
| EP | 1652432 | A2 | 5/2006 |
| EP | 1842426 | A2 | 10/2010 |
| JP | 2-76803 | A | 3/1990 |
| JP | 2004-534789 | | 11/2004 |
| JP | 2010-159247 | | 7/2010 |
| WO | 93/21772 | A2 | 11/1993 |
| WO | 96/32013 | A1 | 10/1996 |
| WO | 97/03562 | A1 | 2/1997 |
| WO | 97/48276 | A1 | 12/1997 |
| WO | 02/100171 | | 12/2002 |
| WO | 2008/142391 | A1 | 11/2008 |
| WO | 2010/001084 | A2 | 1/2010 |
| WO | 2013/168643 | | 11/2013 |

OTHER PUBLICATIONS

HCAPLUS abstract 2006:939018; abstracting CN 1826894 (Sep. 2006).*
HCAPLUS abstract 1990:173972 (1990).*
Rummens, F.H.A., "An improved definition of synergistic and antagonistic effects," Weed Science, vol. 23(1), pp. 4-6 (1975).*
Richer, D.L., "Synergism—a patent view," Pesticide Science, vol. 19, pp. 309-315 (1987).*
2003 NCWSS Report—V.60.
Gianessi et al., "Plant Biotechnology: Potential Impact for Improving Pest Management in European Agriculture", The National Center for Food and Agriculture Policy, Maize-Herbicide-Tolerant Case Study, Dec. 2003.
Harrison, "Confirmation of Shattercane (*Sorghum bicolor*) Resistance to ALS-Inhibiting Herbicides in Ohio", Plant Health Progress, Oct. 21, 2002.
International preliminary report on patentability issued with respect to application No. PCT/JP2012/084281, mail date is Jul. 10, 2014.

* cited by examiner

*Primary Examiner* — John Pak
(74) *Attorney, Agent, or Firm* — Greenblum & Bernstein, P.L.C.

(57) ABSTRACT

At present, various herbicidal compositions have been developed and use, but there are a variety of types of weeds to be controlled, and their development lasts for a long period of time. Thus, a herbicidal composition having a broad herbicidal spectrum, having high activity and having a long-lasting effect has been desired.
The present invention relates to a herbicidal composition comprising (a) nicosulfuron or its salt and (b) S-metolachlor or its salt. According to the present invention, a herbicidal composition having a broad herbicidal spectrum, having high activity and having a long-lasting effect can be provided.

11 Claims, No Drawings

HERBICIDAL COMPOSITION COMPRISING NICOSULFURON OR ITS SALT AND S-METOLACHLOR OR ITS SALT

TECHNICAL FIELD

The present invention relates to a herbicidal composition comprising (a) nicosulfuron or its salt (hereinafter referred to as compound A) and (b) S-metolachlor or its salt (hereinafter referred to as compound B). The present invention further relates to a herbicidal composition which further contains (c) at least one member selected from the group consisting of terbuthylazine, mesotrione, prosulfuron, bicyclopyrone and their salts (hereinafter referred to as compound C).

BACKGROUND ART

Patent Document 1 discloses a herbicidal composition comprising a pyridinesulfonamide compound or its salt and a certain active ingredient. Further, Patent Document 2 discloses a herbicidal composition comprising a chloroacetanilide compound of Formula A and at least one active ingredient selected from the group of substances having various structures. However, Patent Documents 1 and 2 failed to specifically disclose a specific combination of compound A and compound B and synergistic effects obtainable when they are combined.

PRIOR ART DOCUMENTS

Patent Documents

Patent Document 1: JP-A-2-76803
Patent Document 2: JP-A-11-503438

DISCLOSURE OF INVENTION

Technical Problem

At present, many herbicidal compositions have been developed and used, but there are a variety of types of weeds to be controlled, and their development lasts for a long period of time. Thus, a herbicidal composition having a broad herbicidal spectrum, having high activity and having a long-lasting effect has been desired.

Further, compounds A, B and C which are active ingredients in the present invention have some problems that the effects are sometimes unsatisfactory to certain weeds, that their residual activities are sometimes poor and the effects are not satisfactorily maintained for a certain period of time, that weeds having lowered sensitivity to certain herbicides emerge, and that satisfactory effects cannot be practically achieved depending on applications.

Solution to Problem

The present inventors have conducted a study to solve the above problems and as a result, have found it possible to obtain an unexpectedly excellent herbicidal effect by use of compound A and compound B in combination or as the case requires, use of them and further compound C in combination, as compared with a case where the respective compounds are used alone, and thus, the present invention has been accomplished.

That is, the present invention relates to a herbicidal composition comprising compound A and compound B, having a synergistic effect (in this specification, it may sometimes be referred to as a synergistic herbicidal composition). The present invention further relates to such a herbicidal composition further containing compound C having a synergistic effect.

The present invention further relates to a method for controlling undesired plants or inhibiting their growth, which comprises applying a herbicidally effective amount of compound A and a herbicidally effective amount of compound B to the undesired plants or to a place where they grow. The present invention further relates to the method wherein a herbicidally effective amount of compound C is further applied to the undesired plants or to a place where they grow.

Advantageous Effects of Invention

The herbicidal composition of the present invention is capable of controlling a wide range of undesired plants emerging in agricultural fields or non-agricultural fields. It surprisingly represents a synergistic effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on an area where the composition is applied or a surrounding area thereof.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E_1 = \alpha + \beta - (\alpha \times \beta + 100)$$

In a case where three active ingredients are combined, the activity can be similarly calculated as follows.

$$E_2 = (\alpha + \beta + \gamma) - (\alpha\beta + \alpha\gamma + \beta\gamma)/100 + (\alpha\beta\gamma)/10000$$

where $\alpha$: growth inhibition rate when treated with x (g/ha) of herbicide X,
$\beta$: growth inhibition rate when treated with y (g/ha) of herbicide Y,
$\gamma$: growth inhibition rate when treated with z (g/ha) of herbicide Z,
$E_1$: growth inhibition rate expected when treated with x (g/ha) of herbicide X and y (g/ha) of herbicide Y.
$E_2$: growth inhibition rate expected when treated with x (g/ha) of herbicide X, y (g/ha) of herbicide Y and z (g/ha) of herbicide Z.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

As for compound A, nicosulfuron (common name) is 2-(4,6-dimethoxypyrimidin-2-ylcarbamoylsulfamoyl)-N,N-dimethylnicotinamide.

As for compound B, S-metolachlor (common name) is a mixture of (aRS,1S)-2-chloro-6'-ethyl-N-(2-methoxy-1- methylethyl)aceto-o-toluidide (80 to 100%) and (aRS,1R)-2-chloro-6'-ethyl-N-(2-methoxy-1-methylethyl)aceto-o-toluidide (20 to 0%).

As for compound C, terbuthylazine (common name) is $N^2$-tert-butyl-6-chloro-$N^4$-ethyl-1,3,5-triazine-2,4-diamine, and mesotrione (common name) is 2-(4-mesyl-2-nitrobenzoyl)cyclohexane-1,3-dione, and prosulfuron (common name) is 1-(4-methoxy-6-methyl-1,3,5-triazin-2-yl)-3-[2-(3,3,3-trifluoropropyl)phenylsulfonyl]urea, and bicyclopyrone (common name) is 4-hydroxy-3-{2-[(2-methoxyethoxy)methyl]-6-(trifluoromethyl)-3-pyridylcarbonyl}bicyclo[3.2.1]oct-3-en-2-one.

The salt included in compound A, compound B and compound C may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of compound A to compound B cannot generally be defined, as it varies depending upon various conditions such as the type of the formulation, the weather conditions, and the type and the growth stage of the undesired plants, and is, for example, from 1:1.3 to 1:800, preferably from 1:2.5 to 1:200, more preferably from 1:8 to 1:60, particularly preferably from 1:20 to 1:40 by the weight ratio. When nicosulfuron and S-metolachlor are mixed in the above mixing ratio of from 1:20 to 1:40, a particularly excellent effect (for example, a synergistic effect) can be obtained as compared with another mixing ratio.

In a case where the composition further contains compound C, the mixing ratio of compound A to compound C is, for example, from 1:0.006 to 1:400, preferably from 1:0.025 to 1:150 by the weight ratio.

In a case where compound C is terbuthylazine, the mixing ratio of compound A to compound C is, for example, from 1:1 to 1:400, preferably from 1:2.5 to 1:150, more preferably from 1:8 to 1:50 by the weight ratio. By further mixing terbuthylazine with the combination of nicosulfuron and S-metolachlor in the above mixing ratio of nicosulfuron to terbuthylazine of from 1:8 to 1:50, a particularly excellent effect (for example, a synergistic effect) will be obtained as compared with another mixing ratio. Particularly when the mixing ratio of nicosulfuron to S-metolachlor is from 1:20 to 1:40 and the mixing ratio of nicosulfuron to terbuthylazine is from 1:10 to 1:20, a particularly excellent synergistic herbicidal effect against undesired plants, particularly compositae, particularly cocklebur (*Xanthium* spp.), particularly common cocklebur (*Xanthium strumarium* L.) will be obtained.

In a case where compound C is mesotrione, the mixing ratio of compound A to compound C is, for example, from 1:0.05 to 1:100, preferably from 1:0.25 to 1:15, more preferably from 1:0.8 to 1:6 by the weight ratio. By further mixing mesotrione with the combination of nicosulfuron and S-metolachlor in the above mixing ratio of nicosulfuron to mesotrione of from 1:0.8 to 1:6, a particularly excellent effect (for example, a synergistic effect) will be obtained as compared with another mixing ratio. Particularly when the mixing ratio of nicosulfuron to S-metolachlor is from 1:20 to 1:40 and the mixing ratio of nicosulfuron to mesotrione is from 1:1.60 to 1:2.40, a particularly excellent synergistic herbicidal effect against undesired plants, particularly compositae, particularly cocklebur (*Xanthium* spp.), particularly common cocklebur (*Xanthium strumarium* L.) will be obtained.

In a case where compound C is prosulfuron, the mixing ratio of compound A to compound C is, for example, from 1:0.006 to 1:15, preferably from 1:0.025 to 1:5, more preferably from 1:0.08 to 1:2 by the weight ratio. By further mixing prosulfuron with the combination of nicosulfuron and S-metolachlor in the above mixing ratio of nicosulfuron to prosulfuron of from 1:0.08 to 1:2, a particularly excellent effect (for example, a synergistic effect) will be obtained as compared with another mixing ratio. Particularly when the mixing ratio of nicosulfuron to S-metolachlor is from 1:20 to 1:40 and the mixing ratio of nicosulfuron to prosulfuron is from 1:0.1 to 1:1.5, a particularly excellent synergistic herbicidal effect against undesired plants, particularly compositae, particularly cocklebur (*Xanthium* spp.), particularly common cocklebur (*Xanthium strumarium* L.) will be obtained.

In a case where compound C is bicyclopyrone, the mixing ratio of compound A to compound C is, for example, from 1:0.05 to 1:100, preferably from 1:0.25 to 1:15, more preferably from 1:0.8 to 1:10 by the weight ratio. By further mixing bicyclopyrone with the combination of nicosulfuron and S-metolachlor in the above mixing ratio of nicosulfuron to bicyclopyrone of from 1:0.8 to 1:10, a particularly excellent effect (for example, a synergistic effect) will be obtained as compared with another mixing ratio. Particularly when the mixing ratio of nicosulfuron to S-metolachlor is from 1:1 to 1:300 and the mixing ratio of nicosulfuron to bicyclopyrone is from 1:0.1 to 1:20, a particularly excellent synergistic herbicidal effect against undesired plants, particularly leguminosae, particularly rattlepod or rattlebox (*Crotalaria* spp.), particularly sunn-hemp (*Crotalaria iuncea* L.) will be obtained.

The herbicidally effective amounts of compounds A, B and C cannot generally be defined, as they vary depending upon various conditions such as the mixing ratio of compound A to compound B, the mixing ratio of compound A, compound B and compound C, the type of the formulation, the weather conditions, and the type and the growth stage of the undesired plants. However, for example, the following may be mentioned.

Compound A is applied in an amount of from 5 to 150 g/ha, preferably from 10 to 100 g/ha, more preferably from 20 to 60 g/ha, particularly preferably from 30 to 40 g/ha.

Compound B is applied in an amount of from 200 to 4,000 g/ha, preferably from 250 to 2,000 g/ha, more preferably from 500 to 1,200 g/ha, particularly preferably from 800 to 1,200 g/ha.

Compound C is applied in an amount of from 1 to 2,000 g/ha, preferably from 2.5 to 1,500 g/ha.

In a case where compound C is terbuthylazine, compound C is applied in an amount of from 150 to 2,000 g/ha, preferably from 250 to 1,500 g/ha, more preferably from 500 to 1,000 g/ha.

In a case where compound C is mesotrione, compound C is applied in an amount of from 7.5 to 500 g/ha, preferably from 25 to 150 g/ha, more preferably from 50 to 120 g/ha.

In a case where compound C is prosulfuron, compound C is applied in an amount of from 1 to 75 g/ha, preferably from 2.5 to 50 g/ha, more preferably from 5 to 25 g/ha.

In a case where compound C is bicyclopyrone, compound C is applied in an amount of from 7.5 to 500 g/ha, preferably from 25 to 150 g/ha, more preferably from 50 to 150 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a wide range of undesired plants such as annual weeds and perennial weeds. The undesired plants to be controlled by the herbicidal composition of the present invention may, for example, be specifically cyperaceae such as sedge (*Cyperus* spp.) (such as purple nutsedge (*Cyperus rotundus* L.), smallflower umbrella sedge (*Cyperus difformis* L.), yellow nutsedge (*Cyperus esculentus* L.) or amur cyperus (*Cyperus microiria* Steud.)) or spikesedge (*Kylling a* spp.) (such as green kylling a (*Kyllinga brevifolia* Rottb. var. *leiolepis*)); gramineae such as barnyard grass (*Echinochloa* spp.) (such as barnyardgrass (*Echinochloa crus-galli* L.), early watergrass (*Echinochloa oryzicola* vasing.) or Japanese millet (*Echinochloa utilis* Ohwi et Yabuno)), crabgrass (*Digitaria* spp.) (such as summergrass (*Digitaria ciliaris* (Retz.) Koel), large crabgrass (*Digitaria sanguinalis* L.), violet crabgrass (*Digitaria violascens* Link) or Jamaican crabgrass (*Digitaria horizontalis* Willd.)), goosegrass (*Eleusine* spp.) (such as goosegrass (*Eleusine indica* L)), ryegrass (*Lolium* spp.) (such as italian ryegrass (*Lolium multiflorum* Lam.)), foxtail (*Setaria* spp.) (such as green foxtail (*Setaria viridis* (P.) L. Beauv.) or Japanese bristlegrass (*Setaria faberi* Herrm.)), sorghum (*Sorghum* spp.) (such as johnsongrass (*Sorghum halepense* (L.) Pers.) or shattercane (*Sorghum bicolor* (L.) Moench.)), oat (*Avena* spp.) (such as wild oat (*Avena fatua* L.)), brome (*Bromus* spp.) (such as drooping brome (*Bromus tectorum* L.) or japanese brome (*Bromus japonicus* Thunb.)), meadowgrass (*Poa* spp.) (such as annual bluegrass (*Poa annua* L.)), foxtail grass (*Alopecurus* spp.) (such as blackgrass (*Alopecurus myosuroides* Huds.), shortawn foxtail (*Alopecurus aequalis* Sobol. var. *amurensis*)), bermudagrass (*Cynodon dactylon* (L.) Pers.), panic grass (*Panicum* spp.) (such as guinea grass (*Panicum maximum* Jacq.) or fall panicum (*Panicum dichotomiflorum* (L.) Michx.)), signal grass (*Brachiaria* spp.) (such as plantain signal grass (*Brachiaria plantaginea* (LINK) Hitchc.), palisade signal grass (*Brachiaria decumbens* Stapf) or mauritius signal grass (*Brachiaria mutica* (Forssk.) Stapf)), paspalum (*Paspalum* spp.) (such as dallisgrass (*Paspalum dilatatum* Poir.) or vasey's grass (*Paspalum urvillei* Steud.)), itchgrass (*Rottboellia* spp.) (such as itchgrass (*Rottboellia cochinchinensis* (LOUR.) W. D. CLAYTON)), sandbur (*Cenchrus* spp.) (such as southern sandbur (*Cenchrus echinatus* L.)) or wildrye (*Agropyron* spp.) (such as quackgrass (*Agropyron repens* (L.) P. Beauv.)); scrophulariaceae such as persian speedwell (*Veronica persica* Poir.) or corn speedwell (*Veronica arvensis* L.); compositae such as beggar ticks (*Bidens* spp.) (such as hairy beggarticks (*Bidens pilosa* L.), devils berggarticks (*Bidens frondosa* L.) or *Bidens biternata* (Lour.) Merr. et Sherff, beggarticks (*Bidens subalternans* DC.)), dandelion (*Taraxacum* spp.) (such as dandelion (*Taraxacum officinale* Weber)), horseweed (*Conyza* spp.) (such as canadian horseweed (*Conyza canadensis* (L.) Cronquist) or hairy fleabane (*Conyza bonariensis* (L.) Cronq.)), cocklebur (*Xanthium* spp.) (such as common cocklebur (*Xanthium strumarium* L.)), ragweed (*Ambrosia* spp.) (such as annual ragweed (*Ambrosia artemisiifolia* L.)), ragwort (*Senecio* spp.) (such as old-man-in-the-spring (*Senecio vulgaris* L.)), gallant soldier (*Galinsoga* spp.) (such as shaggy soldier (*Galinsoga quadriradiata* Cav.)), sowthistle (*Sonchus* spp.) (such as field sowthistle (*Sonchus arvensis* L.)), or thistle (*Cirsium* spp.) (such as canada thistle (*Cirsium arvense*, (L.) Scop.)); leguminosae such as rattlepod or rattlebox (*Crotalaria* spp.) (such as sunn-hemp (*Crotalaria iuncea* L.)), poison bean (*Sesbania* spp.) (such as rostrate *sesbania* (*Sesbania rostrata* Bremek. & Oberm.) or *sesbania* pea (*Sesbania cannabina* (Retz.) Pers.)), korean lespedeza (*Kummerowia stipulacea* (Maxim.) Makino) or white clover (*Trifolium repens* L.)); caryophyllaceae such as sticky chickweed (*Cerastium qlomeratum* Thuill.), or starwort (*Stellaria* spp.) (such as common chickweed (*Stellaria media* L.)); euphorbiaceae such as garden spurge (*Euphorbia hirta* L.), threeseeded copperleaf (*Acalypha australis* L.) or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.) or henbit (*Lamium amplexicaule* L.); malvaceae such as velvetleaf (*Abutilon theophrasti* MEDIC.) or prickly sida (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea quamoclit* L.), *Ipomoea grandifolia* (DAMMERMANN) O'DONNELL, hairy merremia (*Merremia aeqyptia* (L.) URBAN) or field bindweed (*Convolvulus arvensis* L.); chenopodiaceae such as goosefoot (*Chenopodium* spp.) (such as common lambsquarters (*Chenopodium album* L.)); portulacaceae such as common purslane (*Portulaca oleracea* L.); amaranthaceae such as pigweed (*Amaranthus* spp.) (such as prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L., *Amaranthus patulus* Bertol.), powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L)), ataco (*Amaranthus quitensis* Kunth.) or roughfruit amaranth (*Amaranthus rudis* Sauer.)); solanaceae such as nightshade (*Solanum* spp.) (such as black nightshade (*Solanum niqrum* L.)); polygonaceae such as knotweed (*Polygonum* spp.) (such as spotted knotweed (*Polygonum lapathifolium* L.) or green smartweed (*Polygonum scabrum* MOENCH)); cruciferae such as flexuous bittercress (*Cardamine flexuosa* WITH.), or mustard (*Sinapis* spp.) (such as Charlock (*Sinapis arvensis* L.)); cucurbitaceae such as burcucumber (*Sicyos angulatus* L.); commelinaceae such as common dayflower (*Commelina communis* L.); rosaceae such as mock strawberry (*Duchesnea chrysantha* (Zoll. et Mor.) Miq.); molluqinacea such as carpetweed (*Mollugo verticillata* L.); or rubiaceae such as false cleavers (*Galium spurium* var. *echinospermon* (Wallr.) Hayek) or stickywilly (*Galium aparine* L.).

The herbicidal composition of the present invention is very useful in practical application. For example, the following cases may be mentioned.

(1) It has a remarkable synergistic effect, and has a favorable herbicidal activity even if the doses of the respective compounds A, B and C are small, and accordingly the impact on the surrounding environment can be suppressed.

(2) It can control annual and perennial gramineae such as barnyard grass (*Echinochloa* spp.), crabgrass (*Digitaria* spp.), foxtail (*Setaria* spp.), meadowgrass (*Poa* spp.), oat (*Avena* spp.), wildrye (*Agropyron* spp.), foxtail grass (*Alopecurus* spp.), goosegrass (*Eleusine* spp.), itchgrass (*Rottboellia* spp.), sorghum (*Sorghum* spp.) and panic grass (*Panicum* spp.), which are problematic as noxious weeds in agricultural fields, particularly corn fields.

Noxious weeds may, for example, be weeds which can hardly be controlled by existing herbicides, weeds which are hardly eradicated by spread of rhizomes, or weeds having high reproductivity such that even when their roots are cut e.g. by plowing, they reproduce from part of their roots. They are not only hardly controlled, but make it difficult to harvest crops. In addition, if they are included in the gathered crops, they may cause bad odor in silage, solanine or the like contained in the weeds will lower palatability, or domestic animals may be poisoned with alkaloids or the like contained in the weeds. Accordingly, such weeds cause serious damages to farmers.

(3) It has a high herbicidal activity also against weeds in late leaf stage, such as weeds in 5-leaf stage to heading stage, and such is particularly remarkable for gramineae. In a case where compounds A, B and C are applied alone, the formulations are applied usually by the time of tillering. For example, in the case of summergrass (*Digitaria ciliaris* (Retz.) Koel), large crabgrass (*Digitaria sanguinalis* L.), the formulations are usually applied no later than about 4-leaf stage.

(4) It has a favorable herbicidal activity against gramineae and broad leaf weeds either by foliar application or soil application. It has a long lasting residual activity particularly against gramineae, polygonaceae and compositae.

(5) It has a high herbicidal activity against weeds having lowered sensitivity to herbicides, such as cyperaceae, amaranthaceae, compositae and gramineae. The weeds having lowered sensitivity to herbicides may be weeds having lowered sensitivity to ALS inhibitors, including weeds having lowered sensitivity to sulfonylurea compounds.

The herbicidal composition of the present invention may contain other herbicidally effective component in addition to the above active ingredients, without departing from the intention and the scope of the present invention, whereby the range of weeds to be controlled, the time of application of the composition, the herbicidal activities, etc. may be improved to preferred directions. Other herbicidally effective component includes, for example, the following compounds (by common names including ones under application for approval by ISO, or test codes; common names under application for approval by ISO mean common names before approval by ISO (International Organization for Standardization)). Even when not specifically mentioned here, in a case where such compounds have salts, alkyl esters, hydrates, different crystal forms, various structural isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochior.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone or ethyl[3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, iofensulfuron, or a compound disclosed in the claim of WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid, pyrimisulfan or triafamone; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chiorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, thenylchlor, pethoxamid, acetochlor, propachlor, dimethenamid, dimethenamid-P, propisochloror dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention may be prepared by mixing compound A, compound B and compound C, as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, compound A, compound B and compound C may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.

(1-1) Compound A and compound B are separately formulated, and the formulations are applied as they are, or they are diluted to predetermined concentrations with e.g. water as the case requires, and as the case requires, a spreader (such as a surfactant, a vegetable oil or a mineral oil) is added for application.

(1-2) Compound A and compound B are separately formulated, and the formulations are mixed when diluted to a predetermined concentration with e.g. water, and as the case requires, a spreader (such as a surfactant, a vegetable oil or a mineral oil) is added for application.

(1-3) Compound A and compound B are formulated together, and the formulation is applied as it is, or the formulation is diluted to a predetermined concentration with e.g. water as the case requires, and as the case requires, a spreader (such as a surfactant, a vegetable oil or a mineral oil) is added for application.

(2-1) Compound A, compound B and compound C are separately formulated, and the formulations are applied as they are, or they are diluted to predetermined concentrations with e.g. water as the case requires, and as the case requires, a spreader (such as a surfactant, a vegetable oil or a mineral oil) is added for application.

(2-2) Compound A and compound B are formulated together, and compound C is formulated, and the formulations are applied as they are or diluted to predetermined concentrations with e.g. water as the case requires, and as the case requires, a spreader (such as a surfactant, a vegetable oil or a mineral oil) is added for application.

(2-3) Compound A and compound C are formulated together, and compound B is formulated, and the formulations are applied as they are or diluted to predetermined concentrations with e.g. water as the case requires, and as the case requires, a spreader (such as a surfactant, a vegetable oil or a mineral oil) is added for application.

(2-4) Compound B and compound C are formulated together, and compound A is formulated, and the formulations are applied as they are or diluted to predetermined concentrations with e.g. water as the case requires, and as the case requires, a spreader (such as a surfactant, a vegetable oil or a mineral oil) is added for application.

(2-5) Compound A, compound B and compound C are formulated together, and the formulation is applied as it is or diluted to a predetermined concentration with e.g. water as the case requires, and as the case requires, a spreader (such as a surfactant, a vegetable oil or a mineral oil) is added for application.

In the above application methods (1-1), (1-2) and (2-1) to (2-4), the respective formulations may be mixed when diluted to a predetermined concentration with e.g. water so that they are applied to plants to be controlled simultaneously, or they may be applied continuously or with an appropriate interval. In order to obtain effects of the present invention more effectively, it is preferred to apply compound A and compound B simultaneously or to apply compound A, compound B and compound C simultaneously.

Preferred embodiments of the present invention will be described below, but the present invention is by no means restricted thereto.

(1) A herbicidal composition comprising, as active ingredients, (a) nicosulfuron or its salt and (b) S-metolachlor or its salt.

(2) A method for controlling undesired plants or inhibiting their growth, which comprises applying a herbicidally effective amount of (a) nicosulfuron or its salt and a herbicidally effective amount of (b) S-metolachlor or its salt, to the undesired plants or to a place where they grow.

(3) The herbicidal composition according to (1), wherein the weight ratio of (a) to (b) is within a range of from 1:1.3 to 1:800.

(4) The method according to (2), wherein (a) is applied in an amount of from 5 to 150 g/ha, and (b) is applied in an amount of from 200 to 4,000 g/ha.

(5) The herbicidal composition according to (1), which further contains, as an active ingredient, (c) at least one member selected from the group consisting of terbuthylazine, mesotrione, prosulfuron, bicyclopyrone and their salts.

(6) The method according to (2), wherein a herbicidally effective amount of (c) at least one member selected from the group consisting of terbuthylazine, mesotrione, prosulfuron, bicyclopyrone and their salts is further applied to the undesired plants or to a place where they grow.

(7) The method according to (2) or (6), wherein the undesired plants are undesired plants having lowered sensitivity to herbicides.

(8) The method according to (2) or (6), wherein the undesired plants are plants having lowered sensitivity to ALS inhibitors.

(9) The method according to (2) or (6), wherein by application of the herbicidally active ingredients to the undesired plants or to a place where they grow, they are controlled or their growth is inhibited over at least 40 days, preferably at least 60 days, after the application.

(10) The method according to (2) or (6), wherein by application of the herbicidally active ingredients to pramineae or polygonaceae or to a place where they grow, they are controlled or their growth is inhibited over at least 40 days, preferably at least 60 days, after the application.

(11) The method according to (2) or (6), wherein the undesired plants are undesired plants in 7- or later leaf stage.

(12) The herbicidal composition according to (5), wherein the weight ratio of (a) to (b) is within a range of from 1:1.3 to 1:800, and the weight ratio of (a) to (c) is within a range of from 1:0.006 to 1:400.

(13) The method according to (6), wherein (a) is applied in an amount of from 5 to 150 g/ha, (b) is applied in an amount of from 200 to 4,000 g/ha, and (c) is applied in an amount of from 1 to 2,000 g/ha.

(14) The method according to (2) or (6), wherein the undesired plants are weeds having lowered sensitivity to sulfonylurea compounds.

(15) The herbicidal composition according to (5), wherein (c) is terbuthylazine or its salt, and the weight ratio of (a) to (b) is within a range of from 1:20 to 1:40, and the weight ratio of (a) to (c) is within a range of from 1:10 to 1:20.

(16) The method according to (14), wherein the weeds having lowered sensitivity to sulfonylurea compounds are cyperaceae, amaranthaceae, compositae or gramineae.

(17) The method according to (14), wherein the weeds having lowered sensitivity to sulfonylurea compounds are cyperaceae or gramineae.

(18) The method according to (2) or (6), wherein the undesired plants are compositae or gramineae.

(19) The method according to (16) or (18), wherein the undesired plants (or weeds) are compositae, and the compositae is at least one member selected from the group consisting of cocklebur (*Xanthium* spp.), beggar ticks (*Bidens* spp.), ragweed (*Ambrosia* spp.), horseweed (*Conyza* spp.), gallant soldier (*Galinsoga* spp.), sowthistle (*Sonchus* spp.), dandelion (*Taraxacum* spp.), thistle (*Cirsium* spp.) and ragwort (*Senecio* spp.).

(20) The method according to (16) or (18), wherein the undesired plants (or weeds) are gramineae, and the gramineae is at least one member selected from the group consisting of barnyard grass (*Echinochloa* spp.), signal grass (*Brachiaria* spp.), panic grass (*Panicum* spp.), crabgrass (*Digitaria* spp.), sorghum (*Sorghum* spp.), foxtail (*Setaria* spp.), meadowgrass (*Poa* spp.), oat (*Avena* spp.), wildrye (*Agropyron* spp.), foxtail grass (*Alopecurus* spp.), gooseg-rass (*Eleusine* spp.), ryegrass (*Lolium* spp.), sandbur (*Cenchrus* spp.), brome (*Bromus* spp.) and itchgrass (*Rottboellia* spp.).

(21) The method according to (2) or (6), wherein the undesired plants are at least one member selected from the group consisting of common cocklebur (*Xanthium strumarium* L.), wild oat (*Avena fatua* L.), barnyardgrass (*Echinochloa crus-galli* L.), early watergrass (*Echinochloa oryzicola* vasing.), Japanese millet (*Echinochloa utilis* Ohwi et Yabuno), summergrass (Digitaria ciliaris (Retz.) Koel), large crabgrass (*Digitaria sanquinalis* L.), violet crabgrass (*Digitaria violascens* Link), Jamaican crabgrass (*Digitaria horizontalis* Willd.), sunn-hemp (*Crotalaria juncea* L.), green kylling a (*Kyllinga brevifolia* Rottb. var. *leiolepis*), green foxtail (*Setaria viridis* (P.) L. Beauv.), Japanese bristlegrass (*Setaria faberi* Herrm.), spotted knotweed (*Polygonum lapathifolium* L.), green smartweed (*Polygonum scabrum* MOENCH) and annual bluegrass (*Poa annua* L.).

(22) The method according to (2) or (6), wherein the undesired plants are at least one member selected from the group consisting of common cocklebur (*Xanthium strumarium* L.), wild oat (*Avena fatua* L.), Japanese millet (*Echinochloa utilis* Ohwi et Yabuno), summergrass (*Digitaria ciliaris* (Retz.) Koel), large crabgrass (*Digitaria sanquinalis* L.), sunn-hemp (*Crotalaria juncea* L.), green kylling a (*Kyllinga brevifolia* Rottb. var. *leiolepis*), Japanese bristlegrass (*Setaria faberi* Herrm.), spotted knotweed (*Polygonum lapathifolium* L.) and annual bluegrass (*Poa annua* L.).

(23) The herbicidal composition according to (1), which further contains, as an active ingredient, (c) terbuthylazine or its salt.

(24) The herbicidal composition according to (1), which further contains, as an active ingredient, (c) mesotrione or its salt.

(25) The herbicidal composition according to (1), which further contains, as an active ingredient, (c) prosulfuron or its salt.

(26) The herbicidal composition according to (1), which further contains, as an active ingredient, (c) bicyclopyrone or its salt.

(27) A herbicidal composition comprising (a) and (b), to be used in combination with (c).

(28) A herbicidal composition comprising (a) and (c), to be used in combination with (b).

(29) A herbicidal composition comprising (b) and (c), to be used in combination with (a).

(30) Use of (a), (b) and (c) in combination, to control undesired plants or to inhibit their growth.

(31) Use of a composition comprising (a) and (b), and component (c), in combination, to control undesired plants or to inhibit their growth.

(32) Use of a composition comprising (a) and (c), and component (b), in combination, to control undesired plants or to inhibit their growth.

(33) Use of a composition comprising (b) and (c), and component (a), in combination, to control undesired plants or to inhibit their growth.

(34) The use in combination according to (27) to (33), wherein (c) is terbuthylazine or its salt.

(35) The use in combination according to (27) to (34), to control undesired plants having lowered sensitivity to herbicides or to inhibit their growth.

(36) The use in combination according to (27) to (35), wherein the undesired plants are at least one member selected from the group consisting of common cocklebur (*Xanthium strumarium* L.), wild oat (*Avena fatua* L.), barnyardgrass (*Echinochloa crus-galli* L.), early watergrass (*Echinochloa oryzicola* vasing.), Japanese millet (*Echinochloa utilis* Ohwi et Yabuno), summergrass (*Digitaria ciliaris* (Retz.) Koel), large crabgrass (*Digitaria sanguinalis* L.), violet crabgrass (*Digitaria violascens* Link), Jamaican crabgrass (*Digitaria horizontalis* Willd.), sunn-hemp (*Crotalaria iuncea* L.), green kylling a (*Kylling a brevifolia* Rottb. var. *leiolepis*), green foxtail (*Setaria viridis* (P.) L. Beauv.), Japanese bristlegrass (*Setaria faberi* Herrm.), spotted knotweed (*Polygonum lapathifolium* L.), green smartweed (*Polygonum scabrum* MOENCH) and annual bluegrass (*Poa annua* L.).

EXAMPLES

Now, the present invention will be described in further detail with reference to Examples. However, the present invention is by no means restricted to such specific Examples.

Test Example 1

Upland field soil was put into a 1/1,000,000 ha pot, and seeds of common cocklebur (*Xanthium strumarium* L.) were sown. When the common cocklebur reached 4.3 to 4.8-leaf stage, predetermined amounts of SC agent containing nicosulfuron as an active ingredient (tradename: ONEHOPE NYUZAI, manufactured by Ishihara Sangyo Kaisha, Ltd.), EC agent containing S-metolachlor as an active ingredient (tradename: Dual Gold, manufactured by Syngenta Crop Protection AG), SC agent containing terbuthylazine as an active ingredient (tradename: Click, manufactured by BASF), SC agent containing mesotrione as an active ingredient (tradename: Callisto, manufactured by Syngenta Crop Protection AG) and WG agent containing prosulfuron as an active ingredient (tradename: Peak, manufactured by Syngenta Crop Protection AG) were diluted with water in an amount corresponding to 1,000 L/ha, and applied for foliar treatment by a small sprayer.

On the 22nd day after treatment, the state of growth of the common cocklebur was visually observed to determine the growth inhibition rate in accordance with the following evaluation standard. The growth inhibition rate (%) (measured value) and the growth inhibition rate (%) (calculated value) calculated by the Colby's formula are shown in Table 1.

Growth inhibition rate (%)=0 (equivalent to the non-treated area) to 100 (complete kill)

TABLE 1

| Compound | Dose (g/ha) | Growth inhibition rate (%) of common cocklebur | |
| --- | --- | --- | --- |
| | | Measured value | Calculated value |
| Nicosulfuron | 30 | 0 | — |
| S-metolachlor | 1000 | 0 | — |
| Terbuthylazine | 500 | 10 | — |
| Mesotrione | 50 | 0 | — |
| Prosulfuron | 15 | 88 | — |
| Nicosulfuron + S-metolachlor + Terbuthylazine | 30 + 1000 + 500 | 70 | 10 |
| Nicosulfuron + S-metolachlor + Mesotrione | 30 + 1000 + 50 | 30 | 0 |
| Nicosulfuron + S-metolachlor + Prosulfuron | 30 + 1000 + 15 | 97 | 88 |

Test Example 2

Upland field soil was put into a 1/1,000,000 ha pot, and seeds of Japanese millet (*Echinochloa utilis* Ohwi et Yabuno) were sown. On the next day, predetermined amounts of SC agent containing nicosulfuron as an active ingredient and EC agent containing S-metolachlor as an active ingredient were diluted with water in an amount corresponding to 1,000 L/ha and applied for soil treatment by a small sprayer.

On the 27th day after treatment, the state of growth of the Japanese millet was visually observed to determine the growth inhibition rate. The growth inhibition rate (%) (measured value) and the growth inhibition rate (%) calculated in the same manner as in Test Example 1 are shown in Table 2.

TABLE 2

| Compound | Dose (g/ha) | Growth inhibition rate (%) of Japanese millet | |
| --- | --- | --- | --- |
| | | Measured value | Calculated value |
| Nicosulfuron | 15 | 5 | — |
| S-metolachlor | 500 | 80 | — |
| Nicosulfuron + S-metolachlor | 15 + 500 | 94 | 81 |

Test Example 3

Upland field soil was put into a 1/300,000 ha pot, and seeds of wild oat (*Avena fatua* L.) were sown. On the next day, predetermined amounts of SC agent containing nicosulfuron as an active ingredient, EC agent containing S-metolachlor as an active ingredient, SC agent containing terbuthylazine as an active ingredient, SC agent containing mesotrione as an active ingredient and WG agent containing prosulfuron as an active ingredient were diluted with water in an amount corresponding to 1,000 L/ha and applied for soil treatment by a small sprayer.

On the 14th day after treatment, the state of growth of the wild oat was visually observed to determine the growth inhibition rate. The growth inhibition rate (%) (measured value) and the growth inhibition rate (%) calculated in the same manner as in Test Example 1 are shown in Table 3.

TABLE 3

| Compound | Dose (g/ha) | Growth inhibition rate (%) of wild oat | |
| --- | --- | --- | --- |
| | | Measured value | Calculated value |
| Nicosulfuron | 10 | 10 | — |
| | 100 | 40 | — |
| S-metolachlor | 250 | 15 | — |
| | 2000 | 60 | — |
| Mesotrione | 25 | 0 | — |
| | 150 | 5 | — |
| Terbuthylazine | 250 | 25 | — |
| | 1500 | 5 | — |
| Prosulfuron | 2.5 | 25 | — |
| | 50 | 0 | — |
| Nicosulfuron + S-metolachlor | 10 + 2000 | 95 | 64 |
| | 100 + 250 | 83 | 49 |
| Nicosulfuron + S-metolachlor + Mesotrione | 10 + 2000 + 25 | 83 | 64 |
| | 10 + 2000 + 150 | 85 | 66 |
| | 100 + 250 + 25 | 78 | 49 |
| | 100 + 250 + 150 | 85 | 52 |
| Nicosulfuron + S-metolachlor + Terbuthylazine | 10 + 2000 + 250 | 93 | 73 |
| | 10 + 2000 + 1500 | 95 | 66 |
| | 100 + 250 + 250 | 70 | 62 |
| | 100 + 250 + 1500 | 93 | 52 |
| Nicosulfuron + S-metolachlor + Prosulfuron | 10 + 2000 + 2.5 | 85 | 73 |
| | 10 + 2000 + 50 | 75 | 64 |
| | 100 + 250 + 2.5 | 90 | 62 |
| | 100 + 250 + 50 | 65 | 49 |

Test Example 4

Upland field soil was put into a 1/300,000 ha pot, and seeds of sunn-hemp (*Crotalaria iuncea* L.) were sown. On the next day, predetermined amounts of SC agent containing nicosulfuron as an active ingredient, EC agent containing S-metolachlor as an active ingredient and WP agent containing bicyclopyrone as an active ingredient were diluted with water in an amount corresponding to 1,000 L/ha and applied for soil treatment by a small sprayer.

On the 28th day after treatment, the state of growth of the sunn-hemp was visually observed to determine the growth inhibition rate. The growth inhibition rate (%) (measured value) and the growth inhibition rate (%) calculated in the same manner as in Test Example 1 are shown in Table 4.

TABLE 4

| Compound | Dose (g/ha) | Growth inhibition rate (%) of sunn-hemp | |
|---|---|---|---|
| | | Measured value | Calculated value |
| Nicosulfuron | 10 | 0 | — |
| | 100 | 0 | — |
| S-metolachlor | 250 | 0 | — |
| | 2000 | 0 | — |
| Bicyclopyrone | 25 | 0 | — |
| | 150 | 20 | — |
| Nicosulfuron + S-metolachlor + Bicyclopyrone | 10 + 2000 + 25 | 25 | 0 |
| | 10 + 2000 + 150 | 83 | 20 |
| | 100 + 250 + 25 | 50 | 0 |
| | 100 + 250 + 150 | 45 | 20 |

Test Example 5

Upland field soil was put into a 1/1,000,000 ha pot, and seeds of summergrass (*Digitaria ciliaris* (Retz.) Koel) were sown. When the summergrass reached 7 to 9-leaf stage, predetermined amounts of ONEHOPE NYUZAI (tradename) and Dual Gold (tradename) were diluted with water (corresponding to 300 L/ha) and applied for foliar treatment by a small sprayer.

On the 14th day after treatment, the state of growth of the summergrass was visually observed to determine the growth inhibition rate. The growth inhibition rate (%) (measured value) and the growth inhibition rate (%) calculated in the same manner as in Test Example 1 are shown in Table 5.

TABLE 5

| Compound | Dose (g/ha) | Growth inhibition rate (%) of summergrass | |
|---|---|---|---|
| | | Measured value | Calculated value |
| Nicosulfuron | 15 | 53 | — |
| S-metolachlor | 500 | 0 | — |
| | 2000 | 0 | — |
| Nicosulfuron + S-metolachlor | 15 + 500 | 72 | 53 |
| | 15 + 2000 | 75 | 53 |

As evident from the above Test Example, by mixed use of nicosulfuron and S-metolachlor, a surprising herbicidal activity was exhibited against gramineae in later leaf stage than in a leaf stage in which the grasses can be controlled by application of the respective compounds alone.

Test Example 6

Upland field soil was put into a 1/1,000,000 ha pot, and rhizomes of green kyllinga (*Kyllinga brevifolia* Rottb. var. *leiolepis*) having lowered sensitivity to herbicides were planted. When the height of green kyllinga reached 5 to 7 cm, predetermined amounts of ONEHOPE NYUZAI (tradename) and Dual Gold (tradename) were diluted with water (corresponding to 300 L/ha) and applied for foliar treatment by a small sprayer.

On the 21st day after treatment, the state of growth of the green kyllinga was visually observed to determine the growth inhibition rate. The growth inhibition rate (%) (measured value) and the growth inhibition rate (%) calculated in the same manner as in Test Example 1 are shown in Table 6.

TABLE 6

| Compound | Dose (g/ha) | Growth inhibition rate (%) of green kyllinga | |
|---|---|---|---|
| | | Measured value | Calculated value |
| Nicosulfuron | 30 | 20 | — |
| | 100 | 40 | — |
| S-metolachlor | 500 | 15 | — |
| | 1000 | 45 | — |
| Nicosulfuron + S-metolachlor | 30 + 1000 | 65 | 56 |
| | 100 + 500 | 63 | 49 |

As evident from the above Test Example, by mixed use of nicosulfuron and S-metolachlor, a high activity (synergistic effect) was exhibited against weeds having lowered sensitivity to herbicides as compared with a case where the respective compounds were used alone.

Test Example 7

Upland field soil was put into a 1/500,000 ha pot, and on the next day, predetermined amounts of ONEHOPE NYUZAI (tradename) and Dual Gold (tradename) were diluted with water (corresponding to 300 L/ha) and applied for soil treatment by a small sprayer. On the 14th day after treatment, seeds of Japanese bristlegrass (*Setaria faberi* Herrm) and spotted knotweed, (*Polygonum lapathifolium* L.) were sown.

On the 21st day after sowing, the state of growth of the Japanese bristlegrass and the spotted knotweed was visually observed to determined the growth inhibition rate. The growth inhibition rate (%) (measured value) and the growth inhibition rate (%) calculated in the same manner as in Test Example 1 are shown in Tables 7 and 8.

TABLE 7

| Compound | Dose (g/ha) | Growth inhibition rate (%) of Japanese bristlegrass | |
|---|---|---|---|
| | | Measured value | Calculated value |
| Nicosulfuron | 100 | 33 | — |
| S-metolachlor | 250 | 10 | — |
| Nicosulfuron + S-metolachlor | 100 + 250 | 90 | 39 |

TABLE 8

| Compound | Dose (g/ha) | Growth inhibition rate (%) of spotted knotweed | |
|---|---|---|---|
| | | Measured value | Calculated value |
| Nicosulfuron | 30 | 75 | — |
| S-metolachlor | 1000 | 0 | — |
| Nicosulfuron + S-metolachlor | 30 + 1000 | 90 | 75 |

As evident from the above Test Example, by mixed use of nicosulfuron and S-metolachlor, a long-lasting remarkable herbicidal activity (improvement in the residual activity) was observed as compared with a case where the respective compounds were used alone.

Test Example 8

Upland field soil was put into a 1/1,000,000 ha pot, and seeds of annual bluegrass (*Poa annua* L.) having lowered sensitivity to herbicides were sown. When the annual bluegrass reached 5 to 6-leaf stage, predetermined amounts of ONE-HOPE NYUZAI (tradename) and Dual Gold (tradename) were diluted with water (corresponding to 300 L/ha) and applied for foliar treatment by a small sprayer.

On the 14th day after treatment, the stage of growth of the annual bluegrass was visually observed to determined the growth inhibition rate. The growth inhibition rate (%) (measured value) and the growth inhibition rate (%) calculated in the same manner as in Test Example 1 are shown in Table 9.

TABLE 9

| Compound | Dose (g/ha) | Growth inhibition rate (%) of annual bluegrass | |
|---|---|---|---|
| | | Measured value | Calculated value |
| Nicosulfuron | 100 | 87 | — |
| S-metolachlor | 1000 | 18 | — |
| | 2000 | 28 | — |
| Nicosulfuron + S-metolachlor | 100 + 1000 | 94 | 89 |
| | 100 + 2000 | 99 | 91 |

As evident from the above Test Example, by mixed use of nicosulfuron and S-metolachlor, a high activity (synergistic effect) was exhibited against weeds having lowered sensitivity to herbicides, as compared with a case where the respective compounds were used alone.

INDUSTRIAL APPLICABILITY

According to the present invention, a herbicidal composition having a wide herbicidal spectrum, having high activity and having a long-lasting effect can be provided. Further, according to the present invention, broadening of the herbicidal spectrum particularly against gramineae and application to genetically-modified crops resistant to ALS inhibitors are possible, and an increase in the application site can be expected.

Further, in recent years, emergence of weeds which have acquired resistance due to repeated application of a specific herbicide is problematic. The present invention can meet requirements by practical users that "development of resistance is delayed by use of active ingredients differing in the mechanism in combination".

The entire disclosure of Japanese Patent Application No. 2011-285654 filed on Dec. 27, 2011 including specification, claims and summary is incorporated herein by reference in its entirety.

The invention claimed is:

1. A herbicidal composition comprising, as active ingredients, (a) nicosulfuron or its salt, (b) S-metolachlor or its salt, and (c) at least one member selected from the group consisting of (c1) terbuthylazine, and (c2) prosulfuron, and their salts, wherein the weight ratio of (a) to (b) is within a range of from 1:8 to 1:50, the weight ratio of (a) to (c1) terbuthylazine or its salt is within a range of from 1:2.5 to 1:150, and the weight ratio of (a) to (c2) prosulfuron or its salt is within a range of from 1:0.025 to 1:5.

2. The herbicidal composition according to claim 1, wherein the weight ratio of (a) to (b) is within a range of from 1:20 to 1:40, the weight ratio of (a) to (c1) terbuthylazine or its salt is within a range of from 1:8 to 1:50, and the weight ratio of (a) to (c2) prosulfuron or its salt is within a range of from 1:0.08 to 1:2.

3. A method for controlling undesired plants or inhibiting their growth, which comprises applying a herbicidally effective amount of (a) nicosulfuron or its salt, a herbicidally effective amount of (b) S-metolachlor or its salt, and a herbicidally effective amount of (c) at least one member selected from the group consisting of (c1) terbuthylazine, and (c2) prosulfuron, and their salts to the undesired plants or to a place where they grow, wherein (a) is applied in an amount of from 20 to 60 g/ha, and (b) is applied in an amount of from 500 to 1,200 g/ha, (c1) terbuthylazine or its salt is applied in an amount of from 250 to 1,500 g/ha, and (c2) prosulfuron or its salt is applied in an amount of from 2.5 to 50 g/ha.

4. The method according to claim 3, wherein the undesired plants are undesired plants in 7- or later leaf stage.

5. The method according to claim 3, wherein the undesired plants are undesired plants having lowered sensitivity to herbicides.

6. The method according to claim 4, wherein the undesired plants are plants having lowered sensitivity to ALS inhibitors.

7. The method according to claim 3, wherein the undesired plants are controlled or their growth is inhibited over at least 60 days after the application of the herbicidally active ingredients.

8. The method according to claim 3, wherein the undesired plants are noxious weeds in corn fields.

9. The method according to claim 3, wherein (c1) terbuthylazine or its salt is applied in amount of from 500 to 1,000 g/ha, and (c2) prosulfuron or its salt is applied in an amount of from 5 to 25 g/ha.

10. The method according to claim 3, wherein the (a) is applied in an amount of from 30 to 40 g/ha, (b) is applied in an amount of from 800 to 1,200 g/ha, (c1) terbuthylazine or its salt is applied in an amount of from 500 to 1,000 g/ha, and (c2) prosulfuron or its salt is applied in an amount of from 5 to 25 g/ha.

11. A method for controlling undesired plants or inhibiting their growth, which comprises applying a herbicidally effective amount of (a) nicosulfuron or its salt, a herbicidally effective amount of (b) S-metolachlor or its salt, and a herbicidally effective amount of (c) at least one member selected from the group consisting of (c1) terbuthylazine, and (c2) prosulfuron, and their salts, to the undesired plants or to a place where they grow, wherein the weight ratio of (a) to (b) is within a range of from 1:8 to 1:50, the weight ratio of (a) to (c1) terbuthylazine or its salt is within a range of from 1:2.5 to 1:150, the weight ratio of (a) to (c2) prosulfuron or its salt is within a range of from 1:0.025 to 1:5, and the undesired plants are pancium or brachiaria.

* * * * *